United States Patent [19]

Ritter

[11] Patent Number: 5,512,527
[45] Date of Patent: Apr. 30, 1996

[54] INITIATOR SYSTEMS FOR INITIATING THE POLYMERIZATION OF ETHYLENICALLY UNSATURATED COMPOUNDS AND USE THEREOF

[75] Inventor: Wolfgang Ritter, Haan, Germany

[73] Assignee: Henkel Kommanditgesellschaft auf Aktien, Duesseldorf, Germany

[21] Appl. No.: 278,680

[22] Filed: Jul. 21, 1994

Related U.S. Application Data

[63] Continuation of Ser. No. 859,428, Jul. 27, 1992, abandoned.

[30] Foreign Application Priority Data

Nov. 27, 1989 [DE] Germany ............................ 39 39 164.7

[51] Int. Cl.$^6$ ................................. C09J 5/02; B01J 31/00
[52] U.S. Cl. ............................................ 502/150; 502/172
[58] Field of Search ...................................... 502/150, 172

[56] References Cited

U.S. PATENT DOCUMENTS

| | | | |
|---|---|---|---|
| 4,626,310 | 12/1986 | Ritter | 526/196 |
| 4,676,858 | 6/1987 | Ritter | 526/196 |
| 4,741,848 | 5/1988 | Koch et al. | 252/49.6 |

*Primary Examiner*—Asok Pal
*Attorney, Agent, or Firm*—Ernest G. Szoke; Wayne C. Jaeschke; Daniel S. Ortiz

[57] ABSTRACT

Described are initiator systems for initiating the polymerization of ethylenically unsaturated compounds, which systems have been based on oxygen-reactive organo-boron compounds present in combination with oxygen-resistant carriers; the initiator systems are characterized in that they contain oligoesters of lower hydroxycarboxylic acids as carriers. The invention further relates to the use of these initiator systems in adhesive systems in the technical field, but especially also in the areas of surgery and/or dentistry for curing body-resorbable or body-resistant adhesive agents, cements and/or filler compositions or for forming molded parts of synthetic materials.

21 Claims, No Drawings

INITIATOR SYSTEMS FOR INITIATING THE POLYMERIZATION OF ETHYLENICALLY UNSATURATED COMPOUNDS AND USE THEREOF

This application is a continuation of application Ser. No. 07/859,428 filed on Jul. 27, 1992, now abandoned.

FIELD OF THE INVENTION

The invention relates to new initiator systems for initiating the polymerization of ethylenically unsaturated compounds, said systems being based on oxygen-reactive organoboron compounds present in combination with a carrier material. The new initiator system are basically suitable for any field of application such as, for example, for the commercial sector or a craftman's workshop; however, they have a particular importance for the use in the field of reactive adhesive and/or cement systems in medical and/or dentistry applications, and in this latter sector especially so for dental filling compositions.

DESCRIPTION OF THE INVENTION

There is an extensive literature on polymerization initiation in systems containing ethylenic double bonds by means of organoboron compounds which are activated by the action of oxygen, especially by the action of air, to form the reactive initiator. Pertinent proposals in prior art relate to the area of technical adhesive systems as well as to those components intended for use in the medical area, in particular for surgery and/or dental medicine. In a plurality of previously published proposals made by Applicants there are described the problems involved here and the extensive scientific and practical work, much of which hitherto has also been done by third parties. Reference is made to the printed publications listed hereinbelow and having originated from Applicants and to the third parties' printed material quoted therein, with specific citation of Applicants' respective German Laid-Open Patent Applications (DE-A1), unless explicitly specified otherwise: 30 41 843, 30 41 904 (C2), 31 43 945, 32 01 780, 32 04 504 and, in particular, 32 29 635.

It is particularly the Applicants' last mentioned printed publication that deals with binder systems based on components which are compatible with the body, and especially resorbable by the body, and hence may fulfill functions of an adhesive or cement, respectively, in the field of surgery and/or dental medicine as well as they would be suitable for the manufacture of molded parts to be implanted into the human or animal body and, if so desired, would even be resorbable by the body. In view of the adhesive function, the contemplations includes both bonding endogenous tissue, such as hard tissue, as well as adhesion-bonding such a tissue to plastics and/or metal.

In comparison thereto, it is the object of this invention to find an initiator system for the polymerization initiation, said system being based on oxygen-reactive organoboron compounds and being distinguished by an optimization in production, storage stability and use life and in the behavior in practical use. More particularly, the invention wants to provide carrier systems for admixing same with the organoboron compounds activatable upon the access of air, which carrier systems have a sufficiently low viscosity even in the absence of solvents and/or diluents, therefore ensuring them to be readily incorporated in the material to be polymerized. At the same time, the carrier is intended to stabilize the free radical-forming organo-boron compounds even in the presence of air to such an extent that dwelling in air for an extended period of time of, e.g., several hours or even several days, will be possible and will not result in any substantial loss in activity. Finally —and this is an especially important aspect of practical use —the invention is intended to make available, by way of the new initiator systems, polymerization initiators which in combination with the conventional ethylenically unsaturated adhesive components, for example those based on acrylates or methacrylate, lead to pot-lives sufficient to reliably provide that period of time as required for practical work of at least a few minutes.

The technical solution to this problem underlying the present invention starts from the observation that definitely selected low-viscosity carrier materials derived from oligoesters are suitable to meet the profile of demands as set in an optimum manner. In addition, the oligoester-based carrier materials described hereinbelow are distinguished in that they are physiologically acceptable. They are decomposed in the living organism and, therefore, are acceptable for use in adhesive systems, cements or other synthetic materials used in the fields of medicine and dental medicine.

Accordingly, the invention, in a first embodiment, relates to an initiator system for initiating the polymerization of ethylenically unsaturated compounds, which systems have been based on oxygen-reactive organoboron compounds present in combination with oxygen-resistant carriers; the invention is characterized in that the carrier in said initiator system is constituted by oligoesters of lower hydroxycarboxylic acids.

Thus, hydroxycarboxylic acids having a number of carbon atoms taken from the preferred range of from 2 to 10 are an essential ester-forming component of these carrier materials. Particularly suitable are hydroxycarboxylic acids having from 2 to 6 carbon atoms which may be employed for the oligoester formation in the form of selected definite representatives of this substance class, but also as a mixture of several components from this group. Especially important hydroxycarboxylic acids for forming said carrier are glycolic acid and/or in particular lactic acid which can be used in the form of pre-selected isomers or as a mixture of isomers. Further suitable are the —optionally isomeric —α- or β-hydroxypropionic acids, the —optionally isomeric — α-, β- or γ-hydroxybutyric acid, o-hydroxybenzoic acid (salicylic acid), m-hydroxybenzoic acid and/or p-hydroxybenzoic acid (anisic acid). Both definite isomers and any optional mixtures thereof may be employed.

In a preferred embodiment, the oligoesters of said hydroxycarboxylic acids may have been prepared with the concomitant use of monofunctional and/or polyfunctional reactants causing that oligoesters, terminated with hydroxyl groups or carboxyl groups, of the lower hydroxycarboxylic acids are obtained as the carriers. The concomitant use of said reactants, on the one hand, allows to control the average molecular weight in the ester oligomer and, thus, to adjust the desired viscosity ranges, while, on the other hand, the selection of the functional groups of the concomitantly used co-reactants makes it possible uniformly to have formed terminal hydroxyl groups or terminal carboxyl groups, which per se is not the case a priori in an oligomer of a hydroxycarboxylic acid. If so desired, a concomitant use of pre-selected co-reactants can eliminate reactive terminal groups of the oligoesters so that thereby another possibility is provided of controlling the degree of oligomerization.

Suitable monofunctional co-reactants, more particularly, include monoalcohols and/or monocarboxylic acids, among which the respective compounds having a restricted number of carbon atoms, e.g. up to 12 carbon atoms, and preferably up to 6 carbon atoms, may be preferred. Nevertheless, especially suitable as the carrier material are oligoesters of the described type which have been prepared with the concomitant use of polyhydric alcohols or also of polybasic carboxylic acids. As the polyhydric alcohols there are to be considered especially 2- to 4-functional alcohols, and especially diols such as ethylene glycol and/or 1,2-propane diol, and particularly glycerol as a trihydric alcohol. Suitable polybasic carboxylic acids are, in particular, dicarboxylic acids having from 2 to 10, and preferably from 2 to 6, carbon atoms.

If oligoesters of the described kind are produced by co-condensation of hydroxycarboxylic acids and especially polyhydric alcohols, then oligoesters bearing terminal hydroxyl groups are ultimately formed. The amount of the concomitantly used alcohols —in adjustment with the reaction conditions —determines the average molecular weight of the oligoesters obtained. Analogously, co-condensation of hydroxycarboxylic acids with, more particularly, dicarboxylic acids or reactive derivatives of dicarboxylic acids provides oligoesters having terminal carboxyl groups. As to details, the general knowledge for the preparation of polyesters and copolyesters is applicable here. The concomitant use of monoalcohols and/or monocarboxylic acids results in blocking the terminal carboxyl group or the terminal hydroxyl group of the respective oligomer.

The oligoesters preferred as carriers according to the invention are prepared by reacting one or more of said polyfunctional alcohols or of the appropriate polyfunctional carboxylic acids with hydroxycarboxylic acids of the kind mentioned above in a molar ratio of from about 1:1 to 1:10, and preferably in a range of from about 1:1 to 1:3. The products of this kind may be excellent in that they optimally meet the profile of demands of the teaching according to the invention as outlined above. Thus, for example, lactic acid/ glycerol oligoesters comprising molar ratios of lactic acid/ glycerol within a range of from 1:1 to 5:1, and especially within a range of from 1:1 to 3:1, in the reaction batch are particularly suitable carrier materials within the scope of the teaching according to the invention.

The formation of the oligoesters is a conventional esterification reaction which is conducted in the presence of catalysts in a per se known manner. Suitable esterification catalysts are, especially if the carrier materials are to be used in medical binders, physiologically acceptable acids such as phosphoric acid. The lower hydroxyalkyl carboxylic acids may be employed in the oligo-esterification as monomer compounds, but also in the form or their dimers, for example as a glycolide or a lactide.

The oligoesters of the described kind that are preferred as carrier materials are low-viscosity products having viscosities within a range of up to about 40,000 mPa.s at room temperature, and especially viscosities of up to at most about 25,000 mPa.s at room temperature. The range of from about 10,000 to 20,000 mPa.s may be considered as a particularly suitable viscosity range.

Carriers as described according to the invention are appropriately admixed with the organoboron compounds as initiator components in the absence of the oxygen of the air. The organoboron compounds usable for this purpose are especially the compounds listed in Applicants' protective rights as initially listed in detail. These initiators have in common the high reactivity in the presence of air, while at the same time the tendency for self-ignition thereof is clearly reduced. This enables the initiator system to be easily and safely handled. The organoboron compounds to be used according to the invention, when used in air, exhibit a slow loss in activity. Thus, they may be advantageously used as a separate hardener component in two-component adhesive systems. The boron containing hardeners result in high strengths of the produced adhesion bonds or of the plastics parts formed in situ, respectively. At the same time there is the possibility of controlling the curing rate and, thus, to adapt same to the conditions as desired in practice. Eventually, the structure of the hardener component ensures good adhesion of the adhesive or binder to the endogenous material of the body.

Accordingly, the usable boron compounds include numerous boron alkyls that are known and/or may be prepared in a known manner. Typical representatives of such boron compounds are, for example, 9-bora-bicyclo-[3.3.1]nonane, diisopinocampheyl borane, dicyclohexyl borane, thexylborane (=2,3-dimethyl-2-butyl borane), 3,5-dimethylborinane and diisoamyl borane. Among these compounds, the first mentioned 9-bora-bicyclo[3.3.1]-nonane is preferred for practical reasons.

A review on the feasible methods for preparing suitable boron compounds is found in the monograph by Herbert C. Brown, "Organic Synthesis via Boranes", Publisher John Wiley & Sons, 1975. As the initiators there may further be used products of a hydroboronation of dialkylboranes and olefins. Conceivable olefins are butene, isobutene, hexene, cyclohexene, vinyl chloride, allyl chloride, allyl amine, or also methyl methacrylate, vinyl acetate or methyl crotonate. Among the suitable compounds there may be mentioned, for example, diisopinocampheyl butylboron, thexylcyclohexyl cyclopentylboron, thexyl limonylboron, trinorbornylboron, B-butyl-9-borabicyclo[3.3.1]nonane, B-isobutyl-9-borabicyclo-[3.3.1]nonane, B-2-(4-cyclohexenyl)ethyl-9-borabicyclo-[3.3.1]nonane, B-cyclopropyl-9-borabicyclo-[3.3.1] nonane, B-p-tolyl-9-borabicyclo[3.3.1]nonane, B-tert-butyl-3,5-dimethylborinane. Further suitable are reaction products of 1,2-dihydroxybenzenes with boron hydride (catechol borane) and tri-n-butyl boroxine.

In order to prepare the initiator systems, the organoboron compounds are dissolved in the oligoester-based carrier materials, appropriately with absolute exclusion of oxygen. If required, this step may be accompanied by moderate heating. Thus, for example, to accelerate dissolution it is possible to heat at temperatures of up to 100° C., and preferably up to about 70° C. The concomitant use of inert liquid solvents in the mixing operation may be expedient. Here, the known solvents for organoboron compounds are usable, especially tetrahydrofuran or polyethers such as diethyleneglycol dimethylether, but also volatile esters, halohydrocarbons and the like. With the use of said liquid auxiliary agents, intimate mixtures are prepared; then the auxiliary liquids may be stripped off, and the initiator mixtures can be isolated thereafter. They are appropriately stored in a closed vessel, preferably under an inert gas, for example under nitrogen.

The content of the organoboron compounds in the initiator systems is appropriately chosen so that the boron content of the initiator system is within the range of from about 0.5 to 10% by weight, and preferably within the range of from about 1 to 5% by weight. These values, based on elemental boron, govern the mixing ratios of the organoboron compounds used in the actual case and the carrier material selected according to the invention in response to the nature and molecular size of the organoboron compound. 9-Borabicyclo[3.3.1]nonane has proven to be particularly valuable as the organo-boron compound in practical use.

The initiator systems according to the invention are used in systems that are caused to react by way of a free radical-initiated polymerization and in detail have been described in Applicants' previous printed publications as initially quoted. Thus, there is just briefly summarized here:

Systems based on acrylate and/or methacrylate compounds —hereinbelow designated as (meth)acrylate compounds —may be especially suitable, said systems in particular consisting of the following components:

One or more monomers polymerizable by free radical-initiated polymerization, polymers for improving cohesion and for adjusting the viscosity, active fillers, if desired, for improving the mechanical properties, and the free radical initiator system to initiate the polymerization.

Of outstanding importance as the polymerizable monomers are, more particularly, (meth)acrylate compounds in combination with (meth)acrylic acid. It has been known that the adhesion to bone material of (meth)acrylate adhesives may be enhanced by boronalkyl hardeners —hereto cf., in detail, the literature quoted in DE-A1 32 29 635. In said last-mentioned reference from the literature there have been described binder systems for surgical purposes, which systems are characterized in that they contain, as resorbable (meth)acrylate components, (meth)acrylic acid esters having (meth)acrylate moieties on polyester-oligomer chains comprising hydroxycarboxylic acids and organoboron compounds as initiators, which substances are liquid to solid at room temperature. Adhesive systems of the type described here are especially suitable for the initiator systems as now newly described according to the invention. The appropriate body-resorbable (meth)acrylate components may be used in both the monomer component and in the polymer component usually concomitantly used. However, the teaching of the invention is not restricted to the use of these body-resorbable materials. Typical examples of such polymer components are polymethyl (meth)acrylate copolymers of methyl (meth)acrylate, polychloroprene, chlorosulfonated polyethylene, nitrile rubbers and urethanes which may be used as enforcement and for elastification and at the same time as thickeners. When body-resorbable systems are employed, then in both the ethylenically unsaturated monomer component and the polymer components to be optionally used, hydroxycarboxylic acid moieties, and especially the respective moieties of glycolic acid and/or lactic acid, are essential moieties forming the molecule.

In many cases it may be desirable or required to add further auxiliary materials such as fillers, for example quartz meal or the like. Eventually, it may be desirable to impart color by employing suitable dyes or pigments.

In the synthetic compositions there may be employed, as additional polymerizable constituents, the numerous components containing polymerizable ethylenical double bonds which are conventionally used, for example, in casting resins, fillers and, more particularly, in reactive adhesives. For example, suitable are (meth)acrylic acid compounds with monohydric or polyhydric, and especially dihydric, alcohols, but also other derivatives of (meth)acrylic acid such as the corresponding acid amides which may be substituted at the amide nitrogen atom, for example with hydrocarbyl moieties.

The mixing ratios of the initiator/carrier system according to the invention to the monomer/binder system are within the conventional range. For example, the initiator systems according to the invention may be used in amounts of from 0.5 to 30% by weight, relative to the quantity to be polymerized.

In the following Examples, there are described the preparation of selected lactic acid oligomers, the admixture thereof with 9-BBN (=9-borabicyclo[3.3.1]-nonane), and the use of the initiator systems thus prepared.

EXAMPLES

1. Preparation of the Oligomer

General procedure for preparing the reaction product of lactide with glycerol

The lactide (L(−)-lactide of the company Boehringer, Ingelheim) and glycerol were heated to 195° C. under nitrogen and with stirring in a conventional laboratory apparatus within one hour while catalyzed with 0.5% of phosphoric acid. The mixture was allowed to react at 195° C. for 6 hours and dispensed while hot. The following products were prepared:

| a) | Lactic acid: | glycerol = 3:1 |
|---|---|---|
|    | Charged: | 432 g of lactide = 3 moles |
|    |          | 184 g of glycerol = 2 moles |
|    | Yield    | 610 g = 99% |
| b) | Lactic acid: | glycerol = 2:1 |
|    | Charged: | 1 008 g of lactide = 7 moles |
|    |          | 644 g of glycerol = 7 moles |
|    | Yield    | 1 621 g = 98.2% |

The composition of the resulting products and the properties thereof are set forth in Table 1.

2. Preparation of the Boronalkyl Hardener

General procedure for preparing the boronalkyl hardener from lactic acid oligomers according to 1. and 9-BBN A three-neck flask equipped with stirrer and thermometer was charged with 100 g of the oligomer according to 1.a) or 1.b). After heating to about 50° C., the flask was evacuated with a rotary slide-valve vacuum pump to 1 mbar two times for ten minutes each, and each time with nitrogen re-filled to atmospheric pressure. Then, the amounts set forth in Table 2 of 9-bora[3.3.1]nonane (9-BBN) were added in a nitrogen stream. For improving the process control, 100 ml of THF (stored over $FeCl_2$) were distilled into the reaction mixture through a column head. The reaction mixture was maintained under a nitrogen stream at about 60° C. to 65° C. for 1.5 hours. Then the THF was distilled of at about 60° C. with the use of water-jet pump vacuum, and the residual amounts of THF were withdrawn at 1 mbar.

The reaction product was transferred under a nitrogen stream into a storage vessel and stored in the closed vessel under $N_2$.

The preparation of the hardeners and the properties thereof are compiled in Table 2.

3. Use of the Prepared Oligolactic Acid-Based Boron-alkyls

General procedure

In a beaker, 40 g of polymethacrylic acid methyl ester (PMMA, commercially available powder, Plexigum MB 319, of the company ROHM, Darmstadt) were dissolved with stirring in 45 g of methacrylic acid methyl ester (MMA)

and 5 g of methacrylic acid (MAS). To portions of 10 g each of this mixture there were added with further intensive stirring amounts of between 1.5 and 10% by weight of the boronalkyl initiators described under 2. The pot-lives of the resulting mixtures varied between 4.5 and 9 minutes. Using these adhesives there were bonded within the pot-life sandblasted and degreased iron sheets, and the strengths were measured in the tensile shear test according to DIN 53 281/3 after 24 hours. The results are compiled in Table 3.

In a further test series designed to furnish evidence of the high stability to oxygen of the air of the oligolactic acid-based boronalkyls prepared, they were stored in an open vessel between 72 and 120 hours and then used as hardeners and tested. The pot lives and tensile shear strengths are presented in brackets in Table 3.

TABLE 1

Oligohydroxycarboxylic acids from glycerol and lactide

| Example | Glycerol | Lactide | Consistency at room temperature | Viscosity Epprecht Viscosimeter/MK 4 at room temperature mPa · s | % free lactic acid | % free glycerol | % free acrolein |
|---|---|---|---|---|---|---|---|
| a | 1 | 1.5 | clear, slightly viscous | 18,000 | | | |
| b | 1 | 1 | slightly yellow, slightly viscous | 16,500 | | | |

TABLE 2

Preparation of the initiator components a 1, a 2, b

| No. | Oligomers: lactic Acid: glycerol | Amount of 9-BBN employed: grams per 100 g of substance | Product properties | Amount of boron % by weight |
|---|---|---|---|---|
| a 1 | 3:1 | 41 | homogeneous, colorless, viscous | 3.64 |
| a 2 | 3:1 | 20 | homogeneous, colorless, viscous | 1.78 |
| b | 2:1 | 41 | homogenous, bright yellow, colorless | 3.64 |

TABLE 3

Survey of the measured values of the tensile strength [in N/mm$^2$]

| Monomer adhesive resin g | Hardener component | | Pot Life minutes | Strength to Fe sheets after 24 hours at room temperature N/mm$^2$ | Boron content in the adhesive % by weight |
| | Type | Amount added % by weight | | | |
|---|---|---|---|---|---|
| 10 | a 1 | 1.5 | 9 | 29 | 0.055 |
| 10 | | 3 | 5 (7) | 27 (27) | 0.11 |
| 10 | | 5 | 5 | 32 | 0.18 |
| 10 | | 10 | 4.5 | 26 | 0.36 |
| 10 | a 2 | 1.5 | 9 | 0 | 0.055 |
| 10 | | 3 | 6 (7) | 27 (26) | 0.11 |
| 10 | | 5 | 5 | 27 | 0.18 |
| 10 | | 10 | 4.5 | 25 | 0.36 |
| 10 | b | 1.5 | 9 | 20 | 0.055 |
| 10 | | 3 | 7.5 | 23 | 0.11 |
| 10 | | 5 | 7 | 25 | 0.18 |
| 10 | | 10 | 7 | 22 | 0.36 |

What is claimed is:

1. A storage stable initiator system for initiating the polymerization of ethylenically unsaturated compounds consisting essentially of a mixture of an oxygen-reactive organoboron compound and an oxygen-resistant carrier consisting essentially of oligoesters of lower hydroxy carboxylic acids whereby polymerization initiation ability of the organoboron compound is preserved when exposed to air for at least several hours.

2. The initiator system according to claim 1 wherein said oligoesters consist essentially of residues of hydroxy carboxylic acids having from 2 to 10 carbon atoms.

3. The initiator system according to claim 1 wherein said carrier consists essentially of at least one member selected from the group consisting of hydroxy-group terminated oligoesters of the lower hydroxy carboxylic acids, and carboxyl-group terminated oligoesters of the lower hydroxy carboxylic acids.

4. The initiator system according to claim 1 wherein said carrier consists essentially of oligoesters of lower hydroxy carboxylic and chain terminated with at least one member selected from the group consisting of alcohols and carboxylic acids.

5. The initiator system according to claim 1 wherein said carrier consists essentially of oligoesters formed by the condensation of lower di- or trifunctional alcohols or combinations thereof with the hydroxy carboxylic acids.

6. The initiator system according to claim 1 wherein said carrier consists essentially of oligoesters formed by the condensation of polyfunctional alcohols or polyfunctional carboxylic acids with hydroxy carboxylic acids or their reactive derivatives in a molar ratio of from about 1:1 to about 1:10.

7. The initiator system according to claim 1 wherein said carrier consists essentially of low viscosity oligoesters having viscosities within a range of up to about 40,000 mPa's at room temperature.

8. The initiator system according to claim 1 wherein the mixing ratios of carrier to the organoboron compound are such that the boron content of the initiator system is within the range of from about 0.5 to about 10% by weight.

9. The initiator system according to claim 1 wherein the initiator system containing the organoboron compounds is not self-igniting in air is capable of initiating the polymerization in the presence of air at room temperature or only moderately elevated temperature.

10. The initiator system according to claim 1 wherein the organoboron compounds which comprise alkyl or aryl groups also contain B–H bonds.

11. The initiator system according to claim 1 wherein said initiator contains at least one trialkylboron compound or at least one alkylboron hydride or a combination thereof.

12. The initiator system of claim 1 wherein the polymerization initiation ability of the mixture is preserved when exposed to air for at least 72 hours.

13. The initiator according to claim 2 wherein said hydroxycarboxylic acids have from 2 to 6 carbon atoms.

14. The initiator system according to claim 2 wherein said oligoesters are oligoesters of at least one member selected from the group consisting of glycolic acid and lactic acid.

15. The initiator system according to claim 4 wherein said alcohols are mono- or polyfunctional alcohols and said carboxylic acids are mono- or polyfunctional carboxylic acids.

16. The initiator system according to claim 5 wherein said oligoesters consist essentially of the condensation products of ethylene glycol or glycerol with hydroxy carboxylic acids or their reactive derivatives.

17. The initiator system according to claim 6 wherein said molar ratio is from about 1:1 to about 1:3.

18. The initiator system according to claim 7 wherein the upper limit of said viscosity is 25,000 mPa's at room temperature.

19. The initiator system according to claim 18 wherein the oligoester consists essentially of the condensation product of at least one member selected from the group consisting of glycolic acid and lactic acid having a viscosity not higher than 25,000 mPa's.

20. The initiator system according to claim 8 wherein said mixing ratio is such that the boron content is from about 1 to about 5% by weight.

21. The initiator system according to claim 11 wherein said alkylboron hydride is a dialkylboron hydride.

* * * * *